US011026619B2

(12) United States Patent
Ternes et al.

(10) Patent No.: US 11,026,619 B2
(45) Date of Patent: Jun. 8, 2021

(54) DETERMINING CARDIAC PACING CAPTURE EFFECTIVENESS OF AN IMPLANTABLE MEDICAL DEVICE

(71) Applicant: Cardiac Pacemakers, Inc., St. Paul, MN (US)

(72) Inventors: David J. Ternes, Roseville, MN (US); Qi An, Blaine, MN (US); Pramodsingh H. Thakur, Woodbury, MN (US); Keith R. Maile, New Brighton, MN (US); Sunipa Saha, Shoreview, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 887 days.

(21) Appl. No.: 15/486,095

(22) Filed: Apr. 12, 2017

(65) Prior Publication Data
US 2017/0296086 A1    Oct. 19, 2017

Related U.S. Application Data

(60) Provisional application No. 62/321,913, filed on Apr. 13, 2016.

(51) Int. Cl.
*A61B 5/352*   (2021.01)
*A61B 5/0205*   (2006.01)
(Continued)

(52) U.S. Cl.
CPC ............ *A61B 5/352* (2021.01); *A61B 5/0205* (2013.01); *A61B 5/1116* (2013.01); *A61B 5/318* (2021.01);
(Continued)

(58) Field of Classification Search
CPC ... A61B 5/0456; A61B 5/0205; A61B 5/1116; A61B 5/7285; A61B 5/743; A61B 5/021; A61B 5/024; A61B 5/0816
See application file for complete search history.

(56) References Cited

U.S. PATENT DOCUMENTS 6,192,275 B1   2/2001   Zhu et al.
6,950,704 B1   9/2005   Bradley
(Continued)

OTHER PUBLICATIONS

Hayes, David L. et al. "Cardiac Resynchronization Therapy and the Relationship of Percent Biventricular Pacing to Symptoms and Survival." Heart Rhythm, 8(9):1469-1475.
(Continued)

*Primary Examiner* — Catherine M Voorhees
*Assistant Examiner* — Roland Dinga
(74) *Attorney, Agent, or Firm* — Faegre Drinker Biddle & Reath LLP

(57) ABSTRACT

A cardiac rhythm management system includes at least one sensing component configured to obtain a first physiological parameter signal, an indication of a cardiac response to a stimulation therapy, and temporal information corresponding to the first physiological parameter signal and the cardiac response; and at least one processor configured to: receive the first physiological parameter signal, the indication of the cardiac response, and the temporal information; and to classify the cardiac response into a first cardiac response class to generate a classified cardiac response. The at least one processor also is configured to determine a correlation, based on the temporal information, between the first physiological parameter signal and the classified cardiac response.

17 Claims, 10 Drawing Sheets

(51) Int. Cl.
- *A61B 5/11* (2006.01)
- *A61B 5/00* (2006.01)
- *A61N 1/37* (2006.01)
- *G16H 50/20* (2018.01)
- *G16H 40/67* (2018.01)
- *A61B 7/00* (2006.01)
- *A61B 5/318* (2021.01)
- *A61B 5/024* (2006.01)
- *A61B 5/08* (2006.01)
- *A61B 5/021* (2006.01)

(52) U.S. Cl.
CPC .......... *A61B 5/7264* (2013.01); *A61B 5/7275* (2013.01); *A61B 5/7285* (2013.01); *A61B 5/743* (2013.01); *A61B 7/00* (2013.01); *A61N 1/371* (2013.01); *G16H 40/67* (2018.01); *G16H 50/20* (2018.01); *A61B 5/021* (2013.01); *A61B 5/024* (2013.01); *A61B 5/0816* (2013.01)

(56) References Cited

U.S. PATENT DOCUMENTS

| | | |
|---|---|---|
| 7,912,544 B1 | 3/2011 | Min et al. |
| 8,521,284 B2 | 8/2013 | Kim et al. |
| 8,600,504 B2 | 12/2013 | Hopper et al. |
| 2005/0131477 A1* | 6/2005 | Meyer .................. A61N 1/371 607/27 |
| 2006/0293714 A1* | 12/2006 | Salo .................. A61N 1/36585 607/9 |
| 2007/0049974 A1* | 3/2007 | Li ...................... A61B 5/0464 607/4 |
| 2009/0299205 A1* | 12/2009 | Chow ................ A61B 5/02405 600/518 |
| 2014/0277243 A1 | 9/2014 | Maskara et al. |
| 2017/0196458 A1 | 7/2017 | Ternes et al. |

OTHER PUBLICATIONS

Koplan, Bruce A., et al. "Heart Failure Decompensation and All-Cause Mortality in Relation to Percent Biventricular Pacing in Patients With Heart Failure." Journal of the American College of Cardiology, 53(4):355-360, 2009.

* cited by examiner

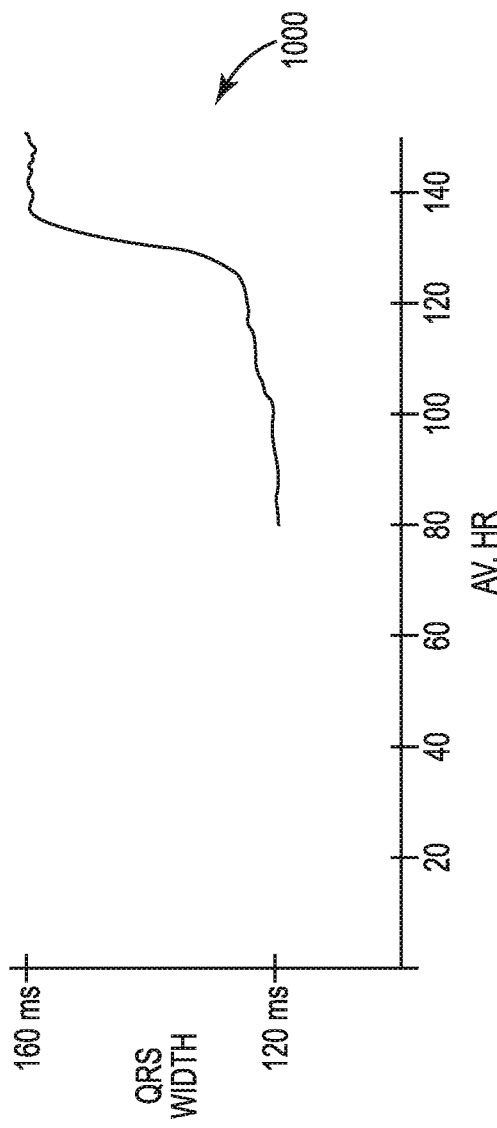
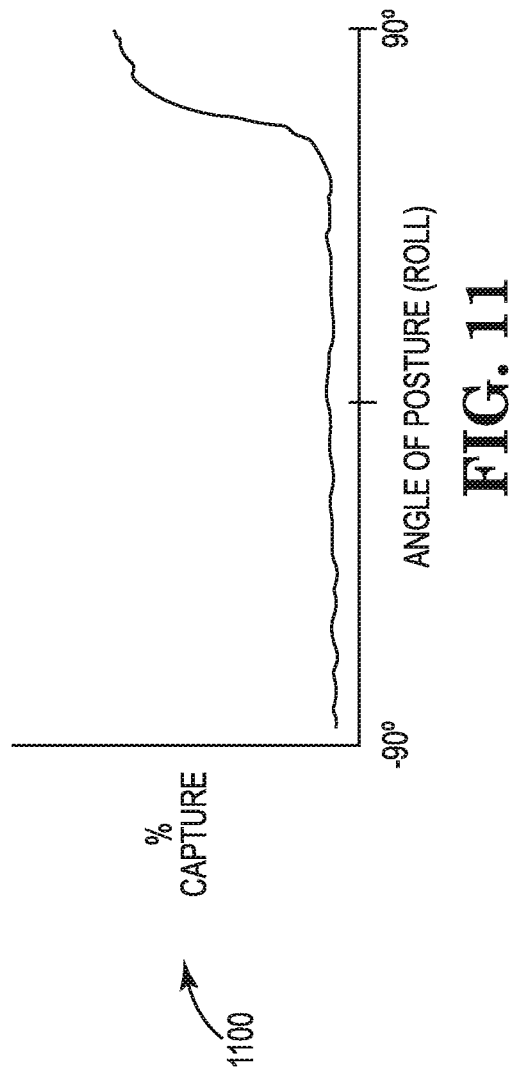

DETERMINING CARDIAC PACING CAPTURE EFFECTIVENESS OF AN IMPLANTABLE MEDICAL DEVICE

CROSS-REFERENCE TO RELATED APPLICATION

This application claims priority to Provisional Application No. 62/321,913, filed Apr. 13, 2016, which is herein incorporated by reference in its entirety.

TECHNICAL FIELD

Embodiments of the present disclosure relate to determining cardiac pacing capture effectiveness of an implantable medical device (IMD).

BACKGROUND

Current IMDs might take frequent physical and device sensor measurements (once a cardiac cycle, every 50 ms, 5 ms, 2.5 ms, etc.) and use that data to deliver closed loop therapy. However, once data has been used for closed-loop therapy it is generally discarded or aggregated into a counter, or histogram, or index (with a few exceptions such as stored EGMs) and large amounts of valuable information may be unavailable for determining pacing capture and other information.

For example, in the context of AF, capture effectiveness tests may be ordered to further an understanding of fusion pacing. As indicated in "Cardiac Resynchronization Therapy and the Relationship of Percent Biventricular Pacing to Symptoms and Survival," Hayes, et. al., Heart Rhythm, Volume 8, Issue 9, 1469-1475, (j.hrthm.2011.04.015), there is an important need to understand CRT and the "relationship of percent biventricular pacing to symptoms and survival." It was found, by Hayes, that the greatest magnitude of reduction in mortality was observed with a biventricular pacing achieved in excess of 98% of all ventricular beats. Atrial fibrillation and native atrial ventricular condition can limit a high degree of biventricular pacing, and incremental increases in mortality benefit are observed with an increasing percentage of biventricular pacing.

Currently, IMDs may provide information including device reports, counters, percentage paced, etc., but the IMD generally does not know if the following occur when pacing: non-capture, fusion, biventricular (BiV) fusion (hybrid between paced and intrinsic), pseudo-fusion (pacing delivered but intrinsic not altered), more complex capture interactions with BiV and left ventricular (LV) multisite pacing (MSP) (e.g., loss of right ventricular pace (RVP) but left ventricular pacing (LVP) capture, loss of LVP but RVP capture, loss of RVP but LV MSP capture, loss of the second LVP in an LV MSP (LVb) capture but other captures, etc.); complex capture interactions with multiple pacing sites in the right ventricle (RV), right atrium (RA), or left atrium (LA); and/or the like.

Conventionally, external monitoring systems like Holter monitors have been used to perform some similar functions, but embodiments of the disclosure facilitate similar levels of data analysis using implanted sensors that are, e.g., less prone to issues such as noise resulting from poorly attached electrodes, limitations on patient activities (e.g., showers), and/or the like. For example, studies have shown a fair prevalence of rate dependent conduction blocks/changes such as, for example, exercise-induced left bundle branch block (EI-LBBB), exercise-induced right bundle branch block (EI-RBBB), worsening conduction in patients with LBBB (at rest and at exercise), PVC, premature atrial contractions (PACs), medication changes, diet changes, and/or the like. A higher risk of death and major cardiac events has been found to be associated with patients experiencing EI-LBBB (and may be found with other conduction changes). However, epidemiologic studies of CRT prevalence have shown that not all LBBB (and other conduction change) patients are at high risk, and when LBBB (and/or other conduction change) is diagnosed matters; as does prior history of co-morbidity. Thus, treatment and risk prevention associated with these conditions may be enhanced by gathering additional information.

Conventional ambulatory patient monitoring systems, and particularly pacing systems, are not configured to identify EI-LBBB, EI-RBBB, V-V conduction changes for those already identified as having wide QRS complex (e.g., widening or narrowing QRS, whether related to cardiac rate, respiration phase, posture, or diet/pharma changes and whether or not is a short-term or long-term trend), post-PVC, post-shock, posture-related conduction changes, changing posture conduction changes, activity-related conduction changes, respiratory-related (e.g., rate, cycle, shallow/deep, hyperventilating, etc.) conduction changes, and/or the like.

SUMMARY

Embodiments include systems, devices, and/or processes for auditing cardiac pacing capture effectiveness of an IMD. In this manner, embodiments may facilitate improving therapy for a patient that is not responding to cardiac resynchronization therapy (CRT), an atrial fibrillation (AF) patient, and/or the like. Embodiments additionally, or alternatively, may include systems, devices, and/or processes for using data from an IMD to identify cardiac conduction issues and patterns. For example, embodiments may include extracting higher-resolution data from an IMD to facilitate identifying cardiac conduction issues and patterns, make programming recommendations, and/or dynamically changing programming, (e.g., dynamically modifying therapy). In this manner, information from IMDs may be used to ascertain specific cardiac behaviors, the nature of anomalies, how the cardiac activity is interrelated with the IMD's operations, and/or the like.

In an Example 1, a cardiac rhythm management system, comprising: at least one sensing component configured to obtain a first physiological parameter signal, an indication of a cardiac response to a stimulation therapy, and temporal information corresponding to the first physiological parameter signal and the cardiac response; and at least one processor configured to: receive the first physiological parameter signal, the indication of the cardiac response, and the temporal information; and classify the cardiac response into a first cardiac response class to generate a classified cardiac response, the first cardiac response class comprising one of a plurality of cardiac response classes, the plurality of cardiac response classes comprising a pace-dominant response class, a non-capture response class, a fusion response class, a pseudo-fusion response class, a bi-ventricle (BiV) fusion response class, a left ventricle (LV) only BiV capture response class, and a right ventricle (RV) only BiV capture response class; determine a correlation, based on the temporal information, between the first physiological parameter signal and the classified cardiac response.

In an Example 2, the system of Example 1, wherein the at least one processor is further configured to generate, based on at least one of the classified cardiac response and the correlation, a therapy programming change recommendation.

In an Example 3, the system of either of Examples 1 or 2, wherein the first physiological parameter comprises at least one of an S1 heart sound and an S2 heart sound.

In an Example 4, the system of Example 3, the first physiological parameter comprising an S1 heart sound, wherein the processor is configured to classify the cardiac response based on the S1 heart sound.

In an Example 5, the system of either of Examples 3 or 4, the first physiological parameter comprising an S2 heart sound, wherein the processor is configured to: determine an S2-R interval; and classify the cardiac response based on the determined S2-R interval.

In an Example 6, the system of either of Examples 1 or 2, wherein the first physiological parameter comprises at least one of a heart rate, a respiration rate, a blood pressure, and a posture.

In an Example 7, the system of any of Examples 1-6, further comprising at least one additional sensing component configured to obtain a second physiological parameter signal, wherein the at least one processor is further configured to verify the classification of the cardiac response based on the second physiological parameter signal.

In an Example 8, the system of Example 7, wherein the second physiological parameter comprises an S1 heart sound.

In an Example 9, the system of any of Examples 1-8, wherein the processor is further configured to: receive a plurality of additional indications of a plurality of additional cardiac responses and the first physiological parameter signal; classify each of the plurality of additional cardiac responses to generate a plurality of additional classified cardiac responses; correlate each of the plurality of additional classified cardiac responses with the first physiological parameter signal to generate a plurality of additional correlations; and cause a display device to present a representation of the plurality of additional correlations.

In an Example 10, the system of Example 9, wherein the representation of the plurality of additional correlations comprises a graph including representations of the first physiological parameter signal and the plurality of additional classified cardiac responses by time of day.

In an Example 11, a cardiac rhythm management system, comprising: at least one sensing component configured to obtain a heart sound signal, a plurality of indications of a plurality of cardiac responses to a stimulation therapy, and temporal information corresponding to the heart sound signal and the cardiac responses; and at least one processor configured to: receive the heart sound signal, the plurality of indications of the plurality of cardiac responses, and the temporal information; and classify each of the plurality of cardiac responses into one of a plurality of cardiac response classes to generate a plurality of classified cardiac responses; determine a correlation, based on the temporal information, between the heart sound signal and the plurality of classified cardiac responses; and cause a display device to present a representation of the correlation.

In an Example 12, the system of Example 11, the plurality of cardiac response classes comprising a pace-dominant response class, a non-capture response class, a fusion response class, a pseudo-fusion response class, a bi-ventricle (BiV) fusion response class, a left ventricle (LV) only BiV capture response class, and a right ventricle (RV) only BiV capture response class.

In an Example 13, the system of either of Examples 11 or 12, wherein the heart sound signal comprises at least one of an S1 heart sound signal and an S2 heart sound signal.

In an Example 14, the system of Example 13, wherein the heart sound signal comprises an S1 heart sound signal, the processor further configured to determine a morphology of the S1 heart sound signal, wherein the processor is configured to classify each of the plurality of cardiac responses based on the morphology of the S1 heart sound signal.

In an Example 15, a method of evaluating an effectiveness of a pacing therapy, the method comprising: obtaining a first physiological parameter signal, an indication of a cardiac response to a stimulation therapy, and temporal information corresponding to the first physiological parameter signal and the cardiac response; classifying the cardiac response into a first cardiac response class to generate a classified cardiac response, the first cardiac response class comprising one of a plurality of cardiac response classes, the plurality of cardiac response classes comprising a pace-dominant response class, a non-capture response class, a fusion response class, a pseudo-fusion response class, a bi-ventricle (BiV) fusion response class, a left ventricle (LV) only BiV capture response class, and a right ventricle (RV) only BiV capture response class; determining a correlation, based on the temporal information, between the first physiological parameter signal and the classified cardiac response; and causing a display device to present a representation of the correlation.

In an Example 16, a cardiac rhythm management system, comprising: at least one sensing component configured to obtain a first physiological parameter signal, an indication of a cardiac response to a stimulation therapy, and temporal information corresponding to the first physiological parameter signal and the cardiac response; and at least one processor configured to: receive the first physiological parameter signal, the indication of the cardiac response, and the temporal information; and classify the cardiac response into a first cardiac response class to generate a classified cardiac response, the first cardiac response class comprising one of a plurality of cardiac response classes, the plurality of cardiac response classes comprising a pace-dominant response class, a non-capture response class, a fusion response class, a pseudo-fusion response class, a bi-ventricle (BiV) fusion response class, a left ventricle (LV) only BiV capture response class, and a right ventricle (RV) only BiV capture response class; determine a correlation, based on the temporal information, between the first physiological parameter signal and the classified cardiac response; and cause a display device to present a representation of the correlation.

In an Example 17, the system of Example 16, wherein the at least one processor is further configured to generate, based on at least one of the classified cardiac response and the correlation, a therapy programming change recommendation.

In an Example 18, the system of Example 16, wherein the first physiological parameter comprises at least one of a heart rate, a respiration rate, a blood pressure, a posture, an S1 heart sound, an S2 heart sound, and a cardiac interval within a cardiac cycle.

In an Example 19, the system of Example 18, the first physiological parameter comprising an S1 heart sound, wherein the processor is configured to classify the cardiac response based on at least one of a morphology of the S1 heart sound and an intensity of the S1 heart sound.

In an Example 20, the system of Example 18, the first physiological parameter comprising an S2 heart sound, wherein the processor is configured to: determine an S2-R interval; and classify the cardiac response based on the determined S2-R interval.

In an Example 21, the system of Example 16, further comprising at least one additional sensing component configured to obtain a second physiological parameter signal, wherein the at least one processor is further configured to verify the classification of the cardiac response based on the second physiological parameter signal.

In an Example 22, the system of Example 21, wherein the second physiological parameter comprises at least one of an S1 heart sound and an S2 heart sound.

In an Example 23, the system of Example 16, wherein the processor is further configured to: receive a plurality of additional indications of a plurality of additional cardiac responses and the first physiological parameter signal; classify each of the plurality of additional cardiac responses to generate a plurality of additional classified cardiac responses; correlate each of the plurality of additional classified cardiac responses with the first physiological parameter signal to generate a plurality of additional correlations; and cause the display device to present a representation of the plurality of additional correlations.

In an Example 24, the system of Example 23, wherein the representation of the plurality of additional correlations comprises a graph including representations of the first physiological parameter signal and the plurality of additional classified cardiac responses by time of day.

In an Example 25, a cardiac rhythm management system, comprising: at least one sensing component configured to obtain a heart sound signal, a plurality of indications of a plurality of cardiac responses to a stimulation therapy, and temporal information corresponding to the heart sound signal and the cardiac responses; and at least one processor configured to: receive the heart sound signal, the plurality of indications of the plurality of cardiac responses, and the temporal information; and classify each of the plurality of cardiac responses into one of a plurality of cardiac response classes to generate a plurality of classified cardiac responses; determine a correlation, based on the temporal information, between the heart sound signal and the plurality of classified cardiac responses; and cause a display device to present a representation of the correlation.

In an Example 26, the system of Example 25, the plurality of cardiac response classes comprising a pace-dominant response class, a non-capture response class, a fusion response class, a pseudo-fusion response class, a bi-ventricle (BiV) fusion response class, a left ventricle (LV) only BiV capture response class, and a right ventricle (RV) only BiV capture response class.

In an Example 27, the system of Example 25, wherein the heart sound signal comprises at least one of an S1 heart sound signal and an S2 heart sound signal.

In an Example 28, the system of Example 27, wherein the heart sound signal comprises an S1 heart sound signal, the processor further configured to determine a morphology of the S1 heart sound signal and/or an intensity of the S1 heart sound signal, wherein the processor is configured to classify each of the plurality of cardiac responses based on the morphology of the S1 heart sound signal and/or the intensity of the S1 heart sound signal.

In an Example 29, the system of Example 27, wherein the heart sound signal comprises an S2 heart sound signal, wherein the processor is configured to: determine an S2-R interval; and classify the cardiac response based on the determined S2-R interval.

In an Example 30, the system of Example 25, wherein the at least one processor is further configured to generate, based on at least one of the classified cardiac response and the correlation, a therapy programming change recommendation.

In an Example 31, a method of evaluating an effectiveness of a pacing therapy, the method comprising: obtaining a first physiological parameter signal, an indication of a cardiac response to a stimulation therapy, and temporal information corresponding to the first physiological parameter signal and the cardiac response; classifying the cardiac response into a first cardiac response class to generate a classified cardiac response, the first cardiac response class comprising one of a plurality of cardiac response classes, the plurality of cardiac response classes comprising a pace-dominant response class, a non-capture response class, a fusion response class, a pseudo-fusion response class, a bi-ventricle (BiV) fusion response class, a left ventricle (LV) only BiV capture response class, and a right ventricle (RV) only BiV capture response class; determining a correlation, based on the temporal information, between the first physiological parameter signal and the classified cardiac response; and causing a display device to present a representation of the correlation.

In an Example 32, the method of Example 31, wherein the first physiological parameter comprises at least one of a heart rate, a respiration rate, a blood pressure, a posture, an S1 heart sound, and an S2 heart sound.

In an Example 33, the method of Example 31, further comprising: obtaining a second physiological parameter signal; and verifying the classification of the cardiac response based on the second physiological parameter signal.

In an Example 34, the method of Example 33, wherein the second physiological parameter comprises at least one of an S1 heart sound and an S2 heart sound.

In an Example 35, the method of Example 31, further comprising: obtaining a plurality of additional indications of a plurality of additional cardiac responses and the first physiological parameter signal; classifying each of the plurality of additional cardiac responses to generate a plurality of additional classified cardiac responses; correlating each of the plurality of additional classified cardiac responses with the first physiological parameter signal to generate a plurality of additional correlations; and causing the display device to present a representation of the plurality of additional correlations.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

FIGS. 4-11 depict illustrative representations of information associated with evaluations of pacing effectiveness that may be presented on a presentation device, in accordance with embodiments of the disclosure.

Figure 1:
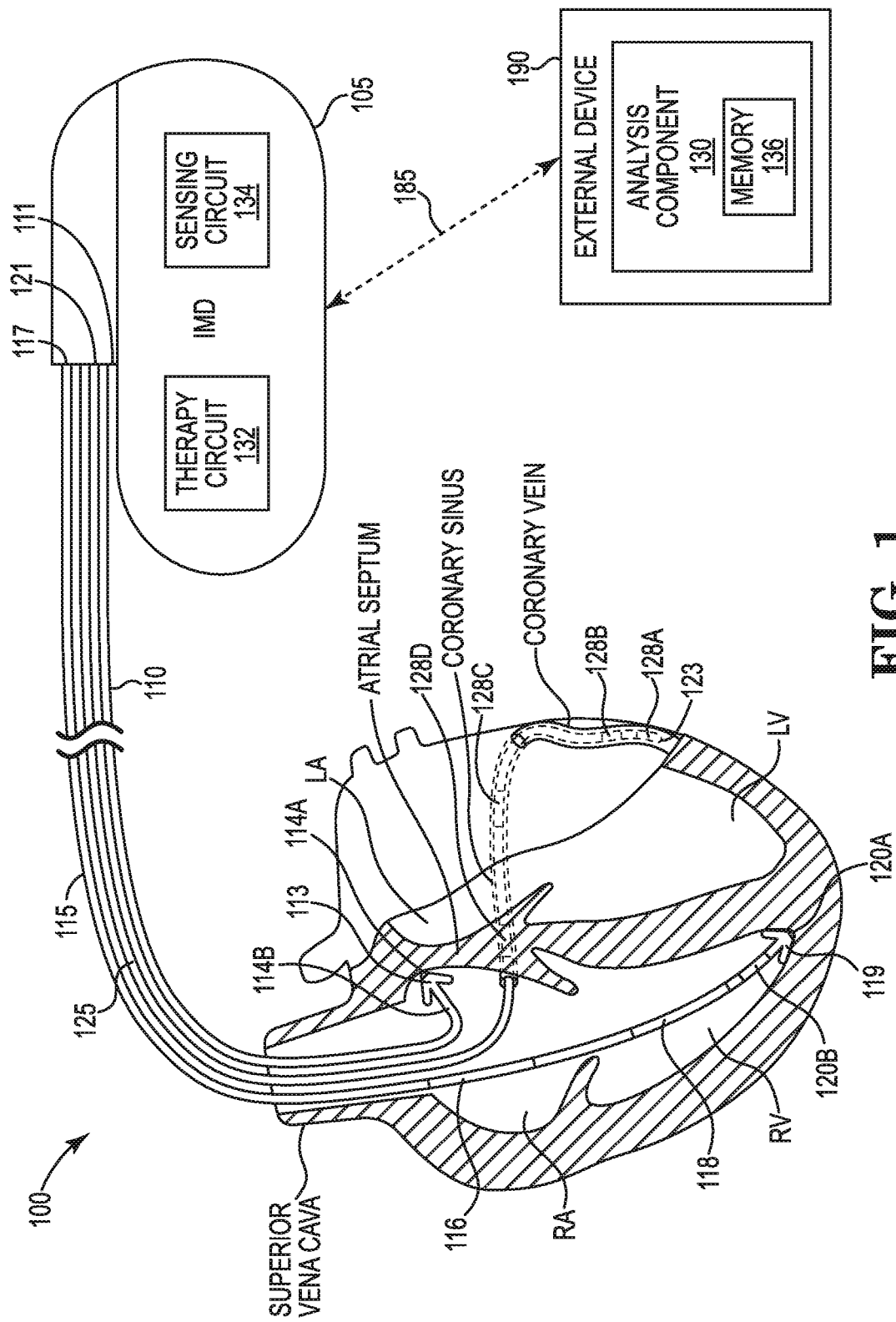
FIG. 1 shows an illustrative medical system, in accordance with embodiments of the disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various steps disclosed herein unless and except when explicitly referring to the order of individual steps. Additionally, a "set" or "group" of items (e.g., inputs, algorithms, data values, etc.) may include one or more items, and, similarly, a subset or subgroup of items may include one or more items.

DETAILED DESCRIPTION

Embodiments include systems, devices, and/or processes for auditing cardiac pacing capture effectiveness of an IMD. In this manner, embodiments may facilitate improving therapy for a patient that is not responding to cardiac resynchronization therapy (CRT), an atrial fibrillation (AF) patient, and/or the like. Embodiments may facilitate, for example, obtaining that data from the IMD to report back pacing effectiveness and possibly make programming recommendations. For example, in embodiments, a clinician may order a capture effectiveness test to be performed on an IMD to facilitate tailoring pacing therapy to the subject. In other embodiments, a capture effectiveness test may be programmatically performed, performed in response to detection of a trigger event, and/or the like.

FIG. 1 shows a medical system 100, including an IMD 105 and an external device 190, with a wireless data connection, telemetry link 185, between IMD 105 and external device 190. In this example of FIG. 1, medical system 100 is a cardiac rhythm management (CRM) system 100. IMD 105 is electrically coupled to a heart through implantable leads 110, 115, and 125. External device 190 communicates with IMD 105 via telemetry link 185.

IMD 105 includes a hermetically sealed can that houses control electronics including an electronic circuit that senses physiological signals and delivers therapeutic electrical pulses. The hermetically sealed can may also function as a can electrode for sensing and/or pulse delivery purposes. IMD 105 may sense one or more cardiac signals, including signals indicative of one or more arrhythmia episodes, and may generate cardiac data representative of the one or more cardiac signals. For example, the control electronics of IMD 105 may sense and store one or more cardiac signals on a continuous basis as facilitated by the higher data storage capacities provided by the rapid improvements in semiconductor technologies. Additionally or alternatively, IMD 105 may store one or more cardiac signals on an episodic basis. In one example, IMD 105 includes a pacemaker that delivers cardiac pacing therapies. In another example, IMD 105 includes a pacemaker and a cardioverter/defibrillator that delivers cardioversion/defibrillation therapies. In various examples, IMD 105 includes one or more devices selected from monitoring devices and therapeutic devices such as a pacemaker, a cardioverter/defibrillator, a neurostimulator, a drug delivery device, and a biological therapy device. In one example, the pacemaker provides for cardiac resynchronization therapy (CRT).

Lead 110 is a right atrial (RA) pacing lead that includes an elongate lead body having a proximal end 111 and a distal end 113. Proximal end 111 is coupled to a connector for connecting to IMD 105. Distal end 113 is configured for placement in the RA in or near the atrial septum. Lead 110 includes an RA tip electrode 114A, and an RA ring electrode 114B. RA electrodes 114A and 114B are incorporated into the lead body at distal end 113 for placement in or near the atrial septum, and are each electrically coupled to IMD 105 through a conductor extending within the lead body. RA tip electrode 114A, RA ring electrode 114B, and/or the can electrode allow for sensing an RA electrogram indicative of RA depolarizations and delivering RA pacing pulses.

Lead 115 is a right ventricular (RV) pacing-defibrillation lead that includes an elongate lead body having a proximal end 117 and a distal end 119. Proximal end 117 is coupled to a connector for connecting to IMD 105. Distal end 119 is configured for placement in the RV. Lead 115 includes a proximal defibrillation electrode 116, a distal defibrillation electrode 118, an RV tip electrode 120A, and an RV ring electrode 120B. Defibrillation electrode 116 is incorporated into the lead body in a location suitable for supraventricular placement in the RA and/or the superior vena cava (SVC). Defibrillation electrode 118 is incorporated into the lead body near distal end 119 for placement in the RV. RV electrodes 120A and 120B are incorporated into the lead body at distal end 119. Electrodes 116, 118, 120A, and 120B are each electrically coupled to IMD 105 through a conductor extending within the lead body. Proximal defibrillation electrode 116, distal defibrillation electrode 118, and/or the can electrode allow for delivery of cardioversion/defibrillation pulses to the heart. RV tip electrode 120A, RV ring electrode 120B, and/or the can of IMD 105 allow for sensing an RV electrogram indicative of RV depolarizations and delivering RV pacing pulses. In various examples, proximal defibrillation electrode 116 and/or distal defibrillation electrode 118 may also be used for sensing the RV electrogram.

Lead 125 is a left ventricular (LV) coronary pacing lead that includes an elongate lead body having a proximal end 121 and a distal end 123. Proximal end 121 is coupled to a connector for connecting to IMD 105. Distal end 123 is configured for placement in the coronary vein. Lead 125 includes an LV tip electrode 128A, a distal LV ring electrode 128B, and two proximal LV ring electrodes 128C and 128D. The distal portion of lead 125 is configured for placement in the coronary sinus and coronary vein such that LV electrodes 128A and 128B are placed in the coronary vein, and LV electrodes 128C and 128D are placed in or near the coronary sinus. LV electrodes 128A and 128B are incorporated into the lead body at distal end 123 and are each electrically coupled to IMD 105 through a conductor extending within the lead body. LV tip electrode 128A, distal LV ring electrode 128B, proximal LV ring electrode 128C, proximal LV ring electrode 128D, and/or the can electrode allow for sensing an LV electrogram indicative of LV depolarizations and delivering LV pacing pulses.

Electrodes from different leads may also be used to sense an electrogram or deliver pacing or cardioversion/defibrillation pulses. For example, an electrogram may be sensed using an electrode selected from RV electrode 116, 118, and 120A-B and another electrode selected from LV electrode 128A-D. The lead configuration including RA lead 110, RV lead 115, and LV lead 125 is illustrated in FIG. 1 by way of example and not by way of restriction. Other lead configurations may be used, depending on monitoring and therapeutic requirements. For example, additional leads may be used to provide access to additional cardiac regions, and leads 110, 115, and 125 may each include more or fewer electrodes along the lead body at, near, and/or distant from the distal end, depending on specified monitoring and therapeutic needs.

In some examples, a wireless sensing and/or therapy system may be used in which, for example, IMD 105 communicates with one or more other implanted devices to facilitate sensing and/or delivering therapy. For example, in embodiments, IMD 105 may be configured to communicate with, and control, one or more leadless pacing seeds implanted in or near the heart. In various examples, IMD 105 senses the one or more cardiac signals using any combination of electrodes, such as those illustrated in FIG. 1, suitable for detection and classification of cardiac responses.

In an example, the IMD 105 can include a therapy circuit 132 that can be electrically coupled to one or more conductors included in one or more of the leads 110, 115, and 125, configured to provide one or more of a voltage or current excitation pulse to the conductor. In an example, the IMD 105 can include a sensing circuit 134 that can be configured to detect a voltage or current developed in response to the excitation provided by the therapy circuit 132. The sensing circuit may also include sensors such as posture sensors, activity sensors, heart sound sensors, and/or the like.

As indicated above, conventional IMDs generally do not know if the following occur when pacing: non-capture, fusion, biventricular (BiV) fusion (hybrid between paced and intrinsic), pseudo-fusion (pacing delivered but intrinsic not altered), more complex capture interactions with BiV and left ventricular (LV) multisite pacing (MSP) (e.g., loss of right ventricular pace (RVP) but left ventricular pacing (LVP) capture, loss of LVP but RVP capture, loss of RVP but LV MSP capture, loss of the second LVP in an LV MSP (LVb) capture but other captures, etc.); complex capture interactions with multiple pacing sites in the right ventricle (RV), right atrium (RA), or left atrium (LA); and/or the like.

In embodiments, this information may be determined by analyzing the evoked response after each pace or by analyzing the EGM waveform of a wide sense vector. The analysis may involve classifying the evoked response and/or EGM waveform based on templates or temporal analysis of the morphology. Multiple wide sense vectors may be used to provide greater specificity. Thus, although some IMDs include beat-to-beat auto-capture functionality, embodiments of the disclosure facilitate enhanced analysis by including classification of the non-capture type and/or fusion type, and facilitating the processing of more sophisticated algorithms, e.g., by providing for non-real-time processing (e.g., processing in a device other than the IMD and/or processing the information at a time other than immediately after pacing).

Additionally, by assessing more than a single cardiac cycle (e.g., as in the case of beat-to-beat auto-capture), embodiments of the disclosure assess the individual cardiac cycle in context of the surrounding beats and may include the opportunity to assess more system wide influences. For example, embodiments may facilitate determining whether a premature ventricular contraction (PVC) interferes with the conduction and pacing effectiveness for a following cardiac cycle or multiple cardiac cycles. Embodiments may also facilitate determining whether a particular posture and/or change in posture causes higher non-capture. Similarly, embodiments may facilitate determining whether the stress of standing, as opposed to reclining, changes conduction enough to lead to more fusion.

IMDs generally also do not know the following: relationship of current cardiac cycle characteristics to those around it (i.e. PVCs, respiratory sinus arrhythmia (RSA), etc.), relationship of current cardiac cycle characteristics to activity, respiration rate, posture changes, etc. (which may affect only RV, the first LVP in an LV MSP (LVa) or LVb, or may affect any other number of paces in an LV MSP such as, e.g., LVc (the third pace), LVd (the fourth pace), etc.), and/or the like.

Capture threshold changes and conduction changes may also be difficult for the IMD to determine and can result from medication changes, rate changes or stress, lead contact changes (particularly LV), activity or posture changes, lead dislodgement, perforation, and/or the like. Embodiments of the disclosure may facilitate determining more transient threshold changes than what current auto-threshold algorithms are capable of determining. Current auto-threshold algorithms typically are performed once per day (or every 21 hours) and are configured to intentionally avoid being performed when the rate is elevated or the patient is active or changing position. In addition, if medication or diet changes thresholds, but only for a few minutes or an hour or so after ingestion, current auto-threshold algorithms might occasionally set the threshold high enough to consistently capture, but that threshold eventually would drop down enough (e.g., because catching the transient threshold rises is fairly random) to put the system in a state such that part of the day the system paces but does not capture. It is understood that patients tend to fare worse if they aren't paced when needed—in particular, it has been shown that CRT pacing percentage is an indicator of outcome (where higher percentages indicate a better outcome), and non-capture/fusion paces are currently included in what the devices count towards CRT pacing percentage. Thus, since embodiments may facilitate discerning non-capture/fusion paces, and thus removing them from the count, the usefulness of the CRT pacing percentage indicator may be improved, thereby facilitating improving pacing regimes for particular patients.

Additionally, embodiments of the disclosure may facilitate identifying conduction changes that lead to more non-capture, fusion, BiV fusion and/or pseudo-fusion (all of which, in greater number, could lead to worsening patient outcome and/or wasted battery/pace energy). Conventional auto-threshold/auto-capture implementations are not configured to identify conduction changes or fusion-type beats, and some are even configured to avoid identifying them. Embodiments of the pace auditing techniques described herein may facilitate identifying these conduction changes, which may be affected by stress, medication, exercise, exercise recovery, posture, cardiac rate, diet (salt, etc.), fluid retention, insulin level, flu, respiratory characteristics (cycle, shallow breathing, hyperventilating, coughing, etc.) and/or the like. Because these influences are transitory and/or cyclic, they would not be included in a percentage pacing number.

In embodiments, upon receiving or initiating an instruction from a user, a program, or the like (e.g., an indication of a trigger event), information obtained by the sensing circuit 134 relating to cardiac response to therapy delivered by leads (e.g., evoked response, EGMs, etc.) may be transmitted to an external device 190 for evaluation. For example, the transmitted information may be analyzed by the external device 190 in context of other physiological information to evaluate the effectiveness of the pacing. In other embodiments, the IMD 105 may do a part, or all of the analysis. External device 190 may include a programmer and/or other components of a patient monitoring system such as, for example, a repeater, a cellular phone, a computing device, and/or the like. External device 190 may include an external therapy and/or sensing device such as, for example, a wearable defibrillator, an external cardiac monitor, and/or the like. External device 190 allows for programming of IMD 105 as well as diagnostic analysis of physiological sensor data and may receive data from IMD 105 representative of signals acquired by IMD 105 via telemetry link 185.

Telemetry link 185 provides for data transmission from IMD 105 to external device 190. Data transmission from IMD 105 to external device 190 may include, for example, physiological data acquired by and stored in IMD 105, therapy history data stored in IMD 105, and data indicating an operational status of IMD 105 (e.g., battery status and lead impedance). The physiological data include the cardiac data representative of the one or more cardiac signals.

Telemetry link 185 also provides for data transmission from external device 190 to IMD 105. This may include, for example, programming IMD 105 to acquire physiological data, programming IMD 105 to perform at least one self-diagnostic test (such as for a device operational status), programming IMD 105 to run a signal analysis algorithm (such as an algorithm implementing tachyarrhythmia detection) and programming IMD 105 to deliver pacing and/or cardioversion/defibrillation therapies.

Telemetry link 185 may include an inductive telemetry link, a far-field radio-frequency telemetry link, another data transfer link or a combination of multiple data transfer links. Telemetry link 185 occurs transcutaneously, i.e., through the patient's tissue, making it particularly useful in a medical implantable device system. For an inductive telemetry link close proximity and proper orientation between the antennas for IMD 105 and external device 190 and will generally improve the coupling between them, but deviation from ideal orientations can still result in suitably reliable data transfer. In any event, as compared to RF wireless communication techniques, and inductive telemetry link may provide lower power consumption for a given volume of data, but may also be more inconvenient for a patient as the external device is secured in close proximity with the internal device during the data transfer. In embodiments, the data transfer link may vary according to a quantity of data to be transferred between IMD 105 and external device 190.

The term "telemetry link" may refer to an ability to communicate some type of information in at least one direction between at least two devices, and should not be understood to be limited to a direct, persistent, or otherwise limited communication channel. That is, according to some examples, the telemetry link 185 may be a persistent communication link, an intermittent communication link, an ad-hoc communication link, and/or the like. The telemetry link 185 may refer to direct communications between IMD 105 and external device 190, and/or indirect communications that travel between IMD 105 and external device 190 via at least one other device (e.g., a repeater, router, hub, cell phone and/or the like). The telemetry link 185 may facilitate uni-directional and/or bi-directional communication between the IMD 105 and external device 190.

External device 190 includes an analysis component 130 that performs an evaluation of information obtained from IMD 105 to assess the effectiveness of a pacing therapy based on characteristics of capture associated therewith. Analysis component 130 further may include computer-readable memory 136 for storing data received from an IMD, such as the continuous or episodic cardiac signals from IMD 105.

The circuit(s) of the CRM system 100 may be implemented using a combination of hardware, software, and/or firmware. In various examples, each element of IMD 105 and external device 190, including its various examples, may be implemented using an application-specific circuit constructed to perform one or more particular functions or a general-purpose circuit programmed to perform such function(s). Such a general-purpose circuit includes, but is not limited to, a microprocessor or portions thereof, a microcontroller or portions thereof, and a programmable logic circuit or portions thereof. For example, analysis component 130 may include a set of computer-executable instructions stored in a memory that, when executed by a processor, causes the processor to perform aspects of embodiments of the functionality of the analysis component 130 described herein.

In embodiments, the memory includes computer-readable media in the form of volatile and/or nonvolatile memory and may be removable, nonremovable, or a combination thereof. The memory may include non-transitory computer-readable media. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. The computer-executable instructions may include, for example, computer code, machine-useable instructions, and the like such as, for example, program components capable of being executed by one or more processors. Program components may be programmed using any number of different programming environments, including various languages, development kits, frameworks, and/or the like.

Figure 2:
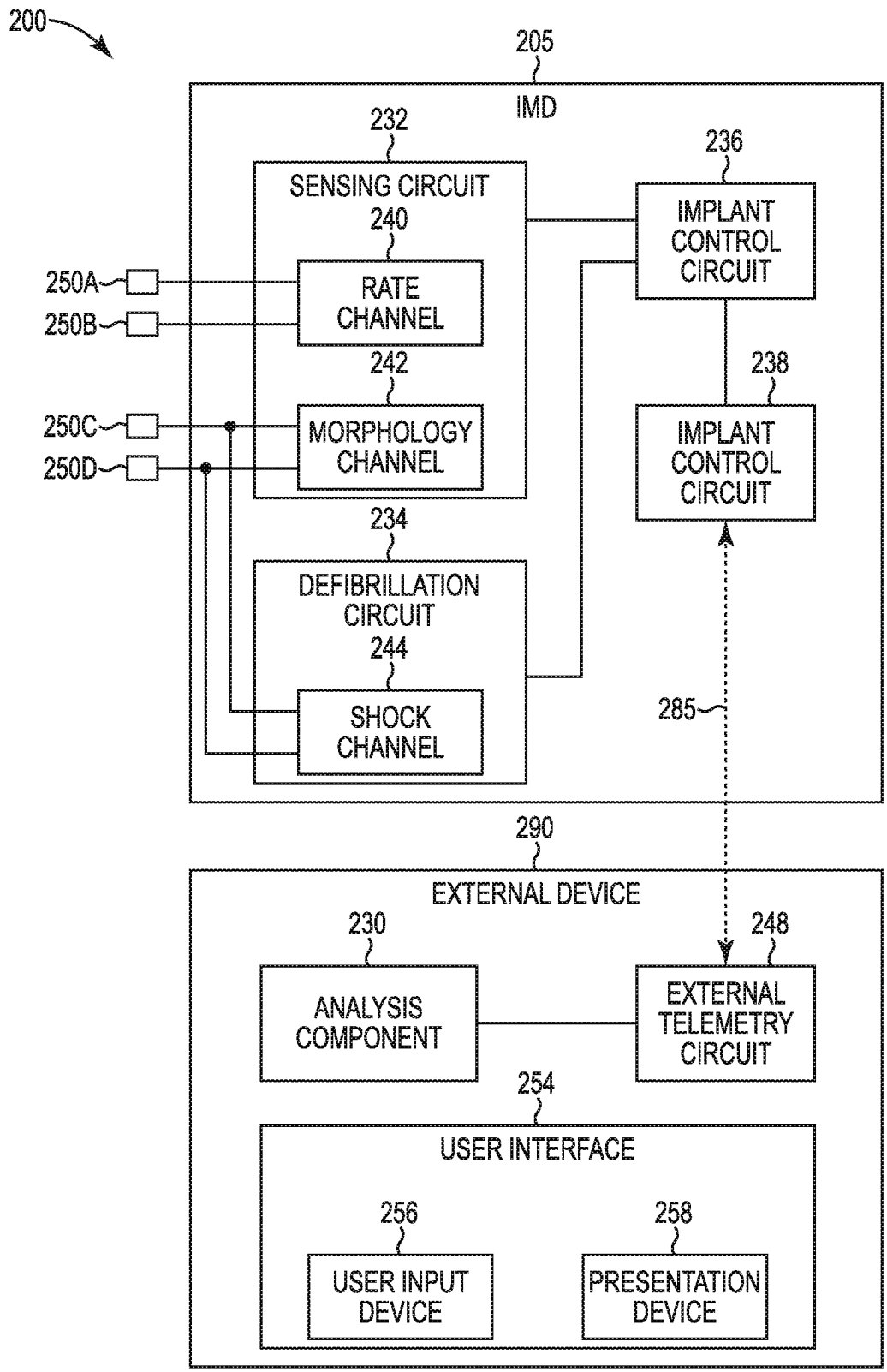
FIG. 2 depicts an illustrative medical device and an illustrative external device, in accordance with embodiments of the disclosure.

FIG. 2 is a block diagram illustrating an example of portions of a circuit of IMD 205 and portions of a circuit of an external device 290 of a medical system 200. IMD 205 represents an example of IMD 105 and includes a sensing circuit 232, a defibrillation circuit 234, control electronics including an implant control circuit 236, and an IMD communication module 238. In embodiments, for example, IMD 205 is an implantable cardioverter defibrillator (ICD).

In other embodiments, IMD 205 may be, or include, a monitoring device, a pacemaker, or a cardiac resynchronization therapy (CRT) device. In embodiments, IMD 205 may include both defibrillation and pacing/CRT capabilities (e.g., a CRT-D device). Sensing circuit 232 includes a rate channel 240 and a morphology channel 242. Rate channel 240 senses a regional cardiac signal through electrodes 250A and 250B for use in heart beat detection. Morphology channel 242 senses a global cardiac signal through electrodes 250C and 250D for use in morphological analysis.

In some examples, rate channel 240 senses a regional ventricular electrogram through an RV tip electrode such as electrode 120A and an RV coil electrode such as electrode 118, and morphology channel 242 senses a global ventricular electrogram through the RV coil electrode and an SVC coil electrode such as electrode 116. In this example, electrode 250A is the RV tip electrode, electrodes 250B and 250C are the same RV coil electrode, and electrode 250D is the SVC coil electrode. In the same or different examples, the SVC coil electrode is electrically connected to the can electrode.

Defibrillation circuit 234 includes a shock channel 244 to deliver cardioversion/defibrillation pulses (shocks). In the illustrated example, shock channel 244 delivers the shocks using the same pair of electrodes as used by morphology channel 242 (so the "morphology channel" is also referred to as the "shock channel"). In an alternative example, a single cardiac signal is sensed for use in heart rate detection and morphology analysis, such as through electrodes 250C and 250D. While this alternative example eliminates the need for sensing two cardiac signals, the example as illustrated in FIG. 2 provides for more robust heart beat detection. Implant control circuit 236 controls the operation of IMD 205 including the sensing of the one or more cardiac signals and the delivery of the shocks. Implant control circuit 236 also includes the physical IMD memory, a non-transitory computer-readable memory, for storing the one or more continuous or episodic cardiac signals. IMD communication module 238 supports the functions of telemetry link 285, including transmitting the cardiac data from IMD 205 to external device 290.

External device 290 represents an example of external device 190 and may represent a hand-held programmer or a clinician's programmer. External device 190 includes analysis component 230, an external telemetry circuit 248, and a user interface 254. Implant telemetry circuit 248 supports the functions of telemetry link 285, including receiving the cardiac data transmitted from IMD 205. User interface 254 includes a user input device 256 and a presentation device 258. User input device 256 receives various commands and parameters from the user for controlling operations of IMD 205 and external device 290. Presentation device 258 presents various patient and device information including representations of cardiac cycle classifications according to capture type, representations of various physiological parameter signals in context of other physiological parameter signals, and/or the like. User interface 254 may be similar to that used for a computer, cell phone, or other hand held electronic device, and may include touchable buttons and a display for example, allowing a user, such as a clinician, to operate the external device 290.

In embodiments, high-resolution data may be extracted from the IMD using a study prescription to audit capture effectiveness by comparing the IMD's interpretation of the situation with the reality. This type of pace auditing may also be useful for IMDs that include auto-capture functionality, to improve the effectiveness thereof. The data may include, for example, at least one EGM channel (e.g., the "wireless" channel), EGM vectors, all of the marker data, as determined by the device (e.g., AF, ventricular tachycardia (VT), ventricular fibrillation (VF), brady tachy response (BTR), device test, etc.), all of the interval data, as determined by the device, and/or the like. Other sensor data may also be captured and utilized in the analysis including, for example, heart sounds, minute ventilation (MV) (raw or filtered, posture, heart sounds, aggregated as breaths per minute, rate or apnea event), posture, and/or the like. In fact, in embodiments, any type of sensor that is being used to determine therapy may be audited in this manner. As an example, MV may be audited as a rate driver by comparing the IMD's interpretation of measurements from the MV and accelerometer against what was desired or expected. In another example, deep brain stimulation (DBS) systems may be audited to reduced tremors, vagus nerve stimulation (VNS) systems may be audited to reduce altered sensed nerve traffic, and/or the like. Examples of systems and methods for facilitating high-resolution gathering are described in U.S. Provisional Patent Application No. 62/276,383, to D. Ternes et al., filed on Jan. 8, 2016, the entirety of which is hereby incorporated herein by reference.

In embodiments, data may be obtained from an IMD by triggering a limited-time system behavior change. Further embodiments include utilizing study prescriptions that specify one or more criteria, procedures, parameters, and/or other aspects of obtaining the data. For example, study prescriptions may facilitate enabling sensor components, obtaining data, analyzing data, batching data obtained by an IMD, communicating the batched data to an external device, reconstructing the batched data at the external device, and/or the like. Study prescriptions may also include instructions for configuring one or more sensors, modifying one or more filters, modifying one or more sensor inputs (e.g. by changing a vector measured by a minute volume (MV) impedance component from focusing on changes in a lung to focusing on stroke volume of the heart), modifying one or more sensing parameters (e.g., sampling rate, sample storage rate, sensing thresholds, sensing durations, etc.), and/or the like.

According to embodiments, a study prescription may be utilized to provide data to an analysis component that adjudicates each cardiac pace for capture or fusion. In embodiments, the analysis component may provide a non-capture analysis report, which may include, for example, rate of occurrence, EGM examples, rate vs. capture analysis, posture vs. capture analysis, intrinsic AV delay vs. capture analysis, time of day vs. capture analysis, CRT or MSP specific analysis, and/or the like. In embodiments, the analysis component may provide a fusion type analysis report, including, for example, breakdown of rate of occurrence, EGM examples, analyses similar to those listed above, and/or the like. Additionally, in embodiments, an external device (e.g., an EMD, a server, a user device, etc.) may provide recommendations, remotely program the IMD, alert physician to need for other patient management changes, and/or the like. That is, for example, embodiments may facilitate using fusion/pseudo-fusion analysis to develop program recommendations or dynamically change therapy parameters such as, for example, changing atrioventricular (AV) node delay to reduce occurrence of fusion/pseudo-fusion. In embodiments, multisite sensing and pacing may be used for cardiac response classification. Illustrative examples of techniques, systems, and methods for using multisite sensing and pacing to classify cardiac response are described in U.S. Pat. No. 8,521,284, to J. Kim et al., issued on Aug. 27, 2013, the entirety of which is hereby incorporated by reference herein.

Heart sounds may be used to confirm capture. In embodiments, S1 morphology may be used to confirm if a pacing pulse is captured or not, as it has been shown that 51 waveforms are different between intrinsic and pacing beats. According to embodiments, for example, 51 heart sound morphology may be used to adjudicate capture (e.g., to identify capture and/or classify capture). For example, an analysis component may be configured to create sensed and confirmed capture templates. S1 heart sounds may then be compared with templates on a beat-by-beat basis. In embodiments, S1 intensity may be used to confirm the capture of a pacing pulse. In embodiments, time intervals (e.g., include R-S1 interval, R-S2 interval, S1-R interval, S2-R interval) between an electrical fiducial (such as an R-wave) and a heart sound can be used to confirm capture of a beat. That is, for example, because R-S1 and R-S2 intervals generally are longer for paced beats than for intrinsic beats, interval thresholds may be used for confirming pacing capture. S2-R interval may also be used as a surrogate for inadequate filling. Embodiments include storing and uploading of the accelerometer channel (heart sounds mode) at the same rate and time-synching the heart sounds to the EGMSs to provide information as to the Electrical/Mechanical (E/M) function such that capture, etc., can be determined. In embodiments, reports may include information regarding the varying E/M delay, the morphology, spectral content, and/or the like. Also, S1, S3, as well as systolic timing intervals can be used to determine the best pacing parameters in acute/ambulatory settings.

For example, S1 morphology may be used to adjudicate whether a beat was captured or not. Device stored sensed (intrinsic) and paced (and confirmed captured) S1 templates may be utilized for this process. On a beat by beat basis, S1 may be compared with the paced/sensed templates to adjudicate whether that particular beat was captured or not. The information can be presented with decision (i.e. 9% sensed, 60% paced and captured, 31% paced and not captured) or as a distribution of correlation (or "match score") across all beats. In another embodiment, time intervals (e.g., R-S1 intervals, R-S2 intervals, S1-R intervals, S2-R intervals) between an electrical fiducial (such as an R-wave) and a heart sound can be used to adjudicate capture of a beat.

As another example, S2-R interval can be used as a surrogate of inadequate filling (an S2-R interval that is too short may indicate that the next R is coming in too early and the ventricle has not had a chance to fill up yet). A distribution of S2-R intervals over the beats of interest may be presented together with population data on diastolic filling variables (such as isovolemic relaxation time, E-wave duration, A-wave duration, diastolic filling time, etc.). Illustrative examples of techniques, systems, and methods for using heart sounds to classify cardiac response are described in U.S. Patent Publication No. 2014/0277243, to B. Maskara et al., filed on Feb. 24, 2014, the entirety of which is hereby incorporated by reference herein.

According to embodiments, some sensor fusion may be analyzed within the IMD, thus facilitating reducing the additional telemetry burden of adding heart sounds. For example, this fusion would know the nominal E/M delay to "synch" to the EGMs and only pull out missed beats, or beat fusion.

In embodiments, the system may be configured to include analysis on RV intrinsics and provide means or recommendations on how to promote RV intrinsics for ICD, BiV pacing for CRT over entire range, and/or the like. In embodiments, a holter characterization of a patient with NO pacing therapy for a period of time (or backup pacing therapy) may be utilized. Additionally, in embodiments, a periodic sweep of pacing to better determine AV delay at all rates and maybe even LVOffset optimization over all rates may be utilized.

Figure 3:
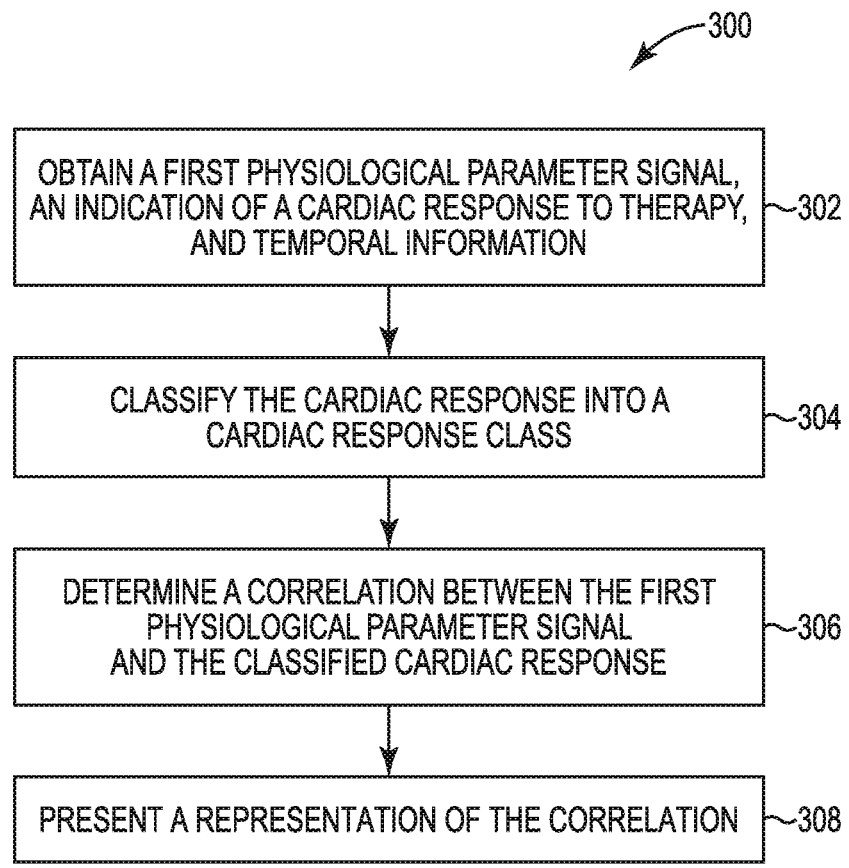
FIG. 3 is a flow diagram depicting an illustrative method of evaluating pacing effectiveness, in accordance with embodiments of the disclosure.

FIG. 3 is a flow diagram depicting an illustrative method 300 of evaluating an effectiveness of a cardiac pacing therapy provided by an implantable medical device (IMD), in accordance with embodiments of the disclosure. According to embodiments, the IMD may be, be similar to, include, or be included in, IMD 105 depicted in FIG. 1 and/or the IMD 205 depicted in FIG. 2. Each of the illustrative steps and functions may be carried out individually or shared by an IMD and/or external device.

Embodiments of the method 300 include obtaining a first physiological parameter signal, an indication of a cardiac response to a stimulation therapy, and temporal information corresponding to the first physiological parameter signal and the cardiac response (block 302). According to embodiments, the first physiological parameter may include, for example, a heart rate, a respiration rate, a blood pressure, a posture, and/or a heart sound (e.g., an S1 heart sound and/or an S2 heart sound).

Embodiments of the method 300 further include classifying the cardiac response into a first cardiac response class to generate a classified cardiac response (block 304). In embodiments, the first cardiac response class may include any one of a number of cardiac response classes, including, for example, a pace-dominant response class, a non-capture response class, a fusion response class, a pseudo-fusion response class, a bi-ventricle (BiV) fusion response class, a left ventricle (LV) only BiV capture response class, and a right ventricle (RV) only BiV capture response class. According to embodiments, the method 300 may include verifying the classification of the cardiac response based on a second physiological parameter signal (e.g., an S1 heart sound, an S2 heart sound morphology as discussed above, and/or time intervals such as R-S1 or R-S2 intervals).

Embodiments of the method 300 further include determining a correlation, based on the temporal information, between the first physiological parameter signal and the classified cardiac response (block 306), and causing a display device to present a representation of the correlation (block 308). According to embodiments, the method 300 may be iterated so as to include, for example, obtaining a number of additional indications of additional cardiac responses; classifying each of the additional cardiac responses to generate additional classified cardiac responses; correlating each of the additional classified cardiac responses with the first physiological parameter signal to generate additional correlations; and causing the display device to present one or more representations of the additional correlations. In embodiments, one or more adjustments to the operation of a therapy circuit and/or a sensing circuit may be made automatically (or via user input) in response to the evaluation described with reference to FIG. 3.

As described above, in embodiments, the method may further include providing a non-capture analysis report, which may include, for example, rate of occurrence, EGM examples, rate vs. capture analysis, posture vs. capture analysis, intrinsic AV delay vs. capture analysis, time of day vs. capture analysis, CRT or MSP specific analysis, and/or the like. The representations of the correlations may be included in the report. In embodiments, one or more pieces of information (e.g., representations of correlations, etc.)

may be presented on a presentation device (e.g., a display), as part of a report, or in addition to inclusion in a report. The report may take the form of any rendering of information such as, for example, an electronic file, a printed (hardcopy) report, a database, and/or the like. In embodiments, any number of different portions of the report may be able to be manipulated (e.g., edited, filtered, etc.) by a user.

Figure 4:
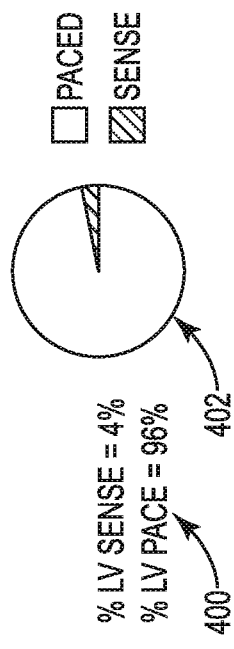
Figure 5:
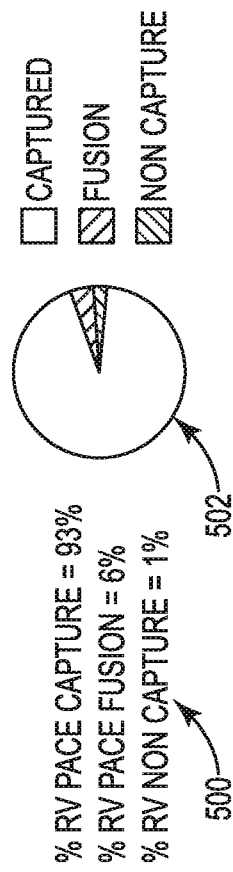
Figure 6:
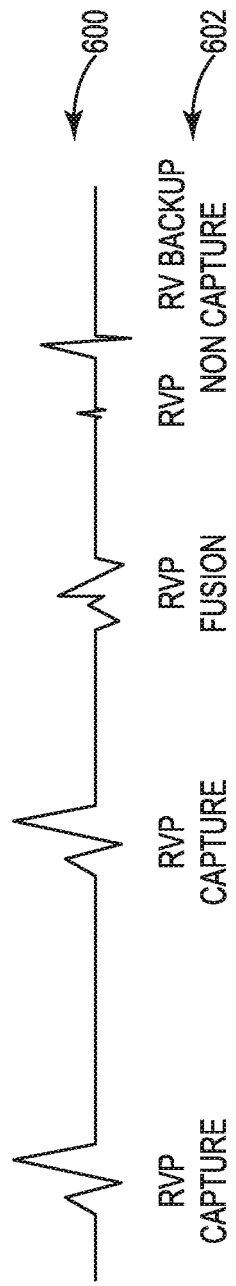

The representations of correlations may be presented with or without representations of classified cardiac responses and/or other physiological parameter signals. FIGS. 4-11 depict various examples of representations of information such as classified cardiac response information and correlation information that may be presented (e.g., via a presentation device, a printed report, etc.). For example, FIGS. 4-6 depict representations of classification information associated with a cardiac cycle, in accordance with embodiments of the disclosure.

As shown in FIG. 4, a representation may indicate, for example, that during the cardiac cycle, the percentage of LV sense recorded was 4%, as compared to 96% LV pace. Text 400 and/or a graphical representation 402 (in this case, a pie chart) may be used to convey this information. As shown in FIG. 5, a representation may include text 500 and/or a graphical representation 502 indicating the distribution of cardiac response classifications for a cardiac cycle. In embodiments, a user such as a clinician may take some action based upon seeing the representations of information 400, 402, 502. That is, for example, if % LV Sense is relatively high, the clinician might adjust AV delay or LV offset to try to promote additional pacing. However, the clinician may not understand, from the example representations, why, or under what circumstances, the LV senses occurred. In another example, if % RV NonCapture is relatively high, the clinician might increase the stimulation amplitude, whereas, if % RV Fusion is relatively high, the clinician might shorten AV delay to promote better capture, or might lengthen AV delay to promote more intrinsic activity.

According to embodiments, classifying each cardiac cycle by type of capture and presenting that information "real-time" (e.g., during or shortly after the cardiac cycle) may provide additional information to a clinician. For example, as shown in FIG. 6, an electrogram 600 may be presented as a real-time, moving waveform. Annotations 602 may be presented along with the electrogram 600 to indicate the class of capture type associated with each beat. Providing information similar to that depicted in FIG. 6 may be useful, for example, in performing an amplitude threshold test, as the clinician would be able to readily identify non-capture situations correlated to certain amplitudes. In embodiments, the electrogram 600 may also be annotated with the amplitude to facilitate such an analysis. Additionally, in embodiments, presenting "real-time" fusion information (that is, information associated with cardiac responses classified as fusion capture types) may facilitate performing a test having a purpose of setting AV delay or LV offset.

Figure 7:
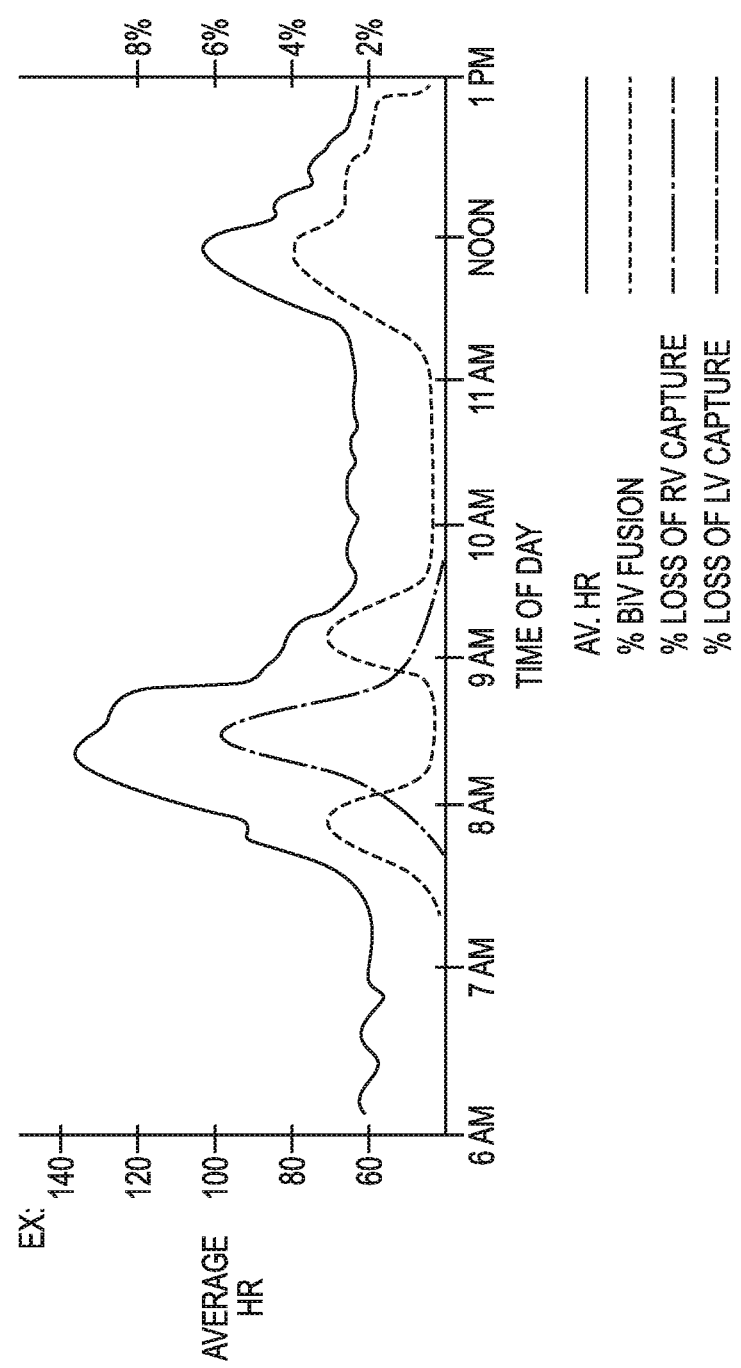

Although presenting information such as that depicted in FIGS. 4-6 may be useful in facilitating some types of decisions, embodiments of the disclosure include presenting correlation information that may be more readily actionable. For example, FIG. 7 depicts an illustrative graphical representation 700 of correlation information associated with an average heart rate, % BiV fusion, % loss of RV capture, % loss of LV capture, and time of day. In embodiments, a clinician may, for example, be able to glance at the graphical representation 700 and determine, from the presented information, that shortening the LV offset (in a CRT system that is configured to enable dynamic LV offset) at higher rates would maintain CRT effectiveness. If the CRT system does not offer dynamic LV offset, the clinician may be able to determine, from the presented information, that pulling in AV delay at higher rates may maintain CRT effectiveness.

Figure 8:
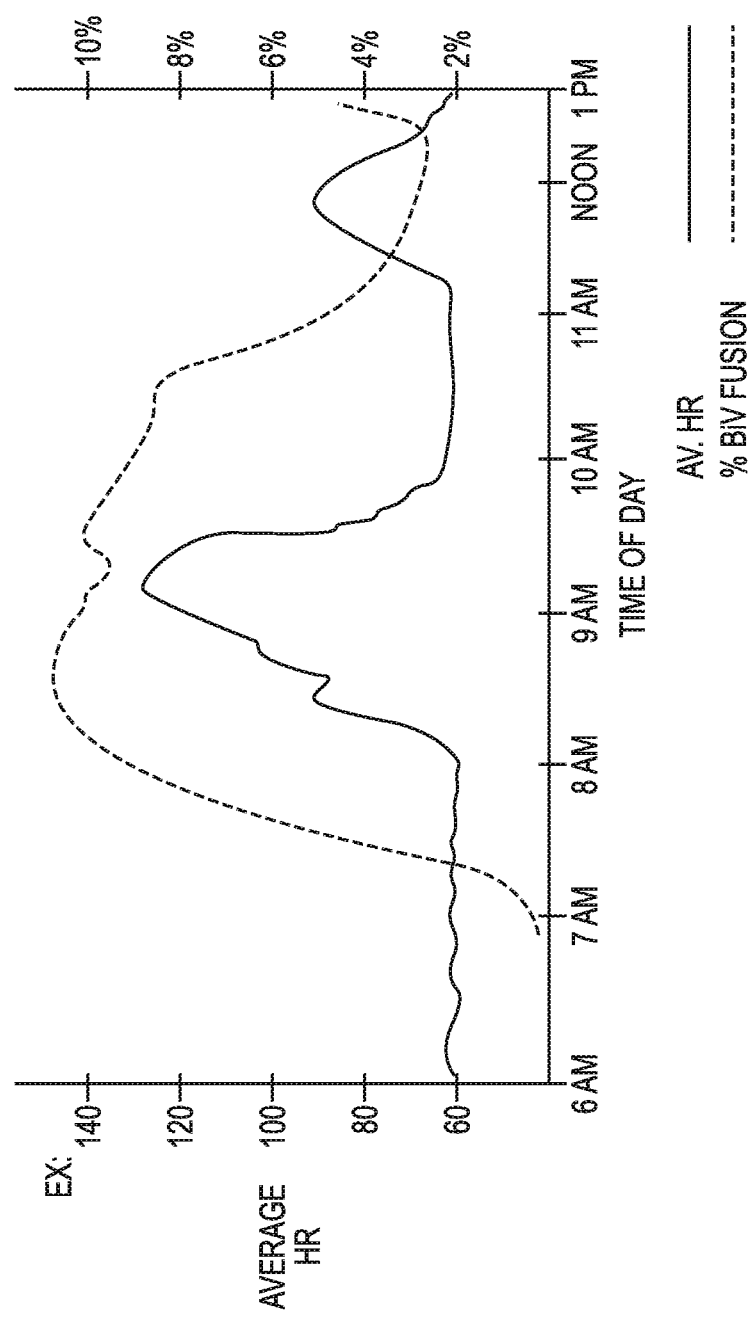

Another illustrative example of a graphical representation 800 of correlation information is depicted in FIG. 8. The graphical representation 800 depicts correlation information associated with an average heart rate, % BiV fusion, and time of day. In embodiments, a clinician may, for example, be able to glance at the graphical representation 800 and determine, from the presented information, that % BiV fusion does not appear to have a strong correlation with heart rate, but does appear to have a strong correlation with time of day. This may, for instance, prompt the clinician to ask the patient when the patient took medication and, based on the answer (e.g., 7 am), may have useful information for determining whether to adjust the medication and/or programmed pacing parameters.

Figure 9:
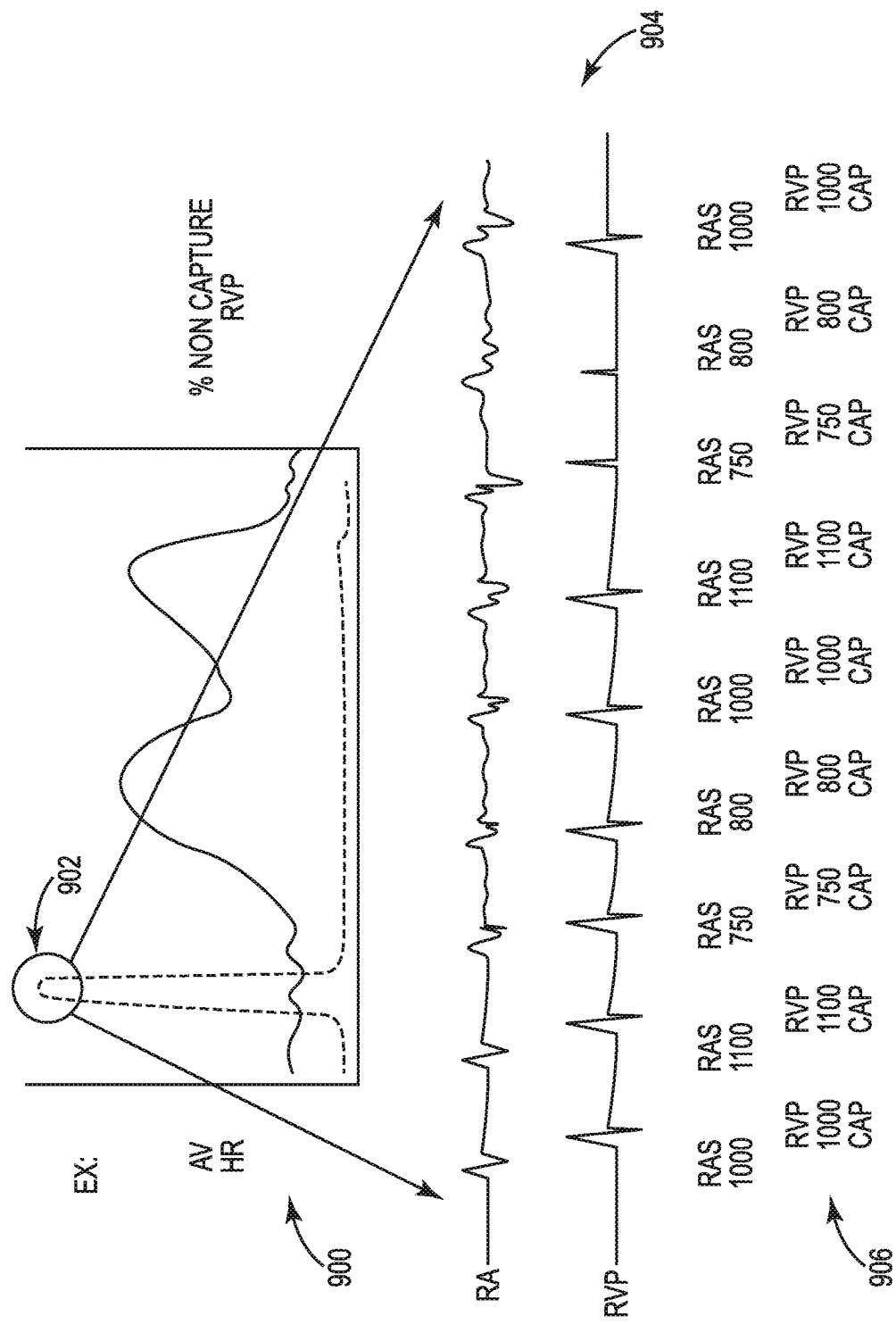

In embodiments, graphical representations may be interactive. That is, for example, a user (e.g., a clinician) may be able to select or otherwise manipulate a portion of a graphical representation to cause the system to present additional information. For example, FIG. 9 depicts an illustrative graphical representation 900 of correlation information associated with average heart rate and % non-capture of a right ventricular pacing pulse (RVP). In response to a user selection (e.g., using a mouse, a finger or stylus, etc.) of a region of interest 902, a set 904 of electrogram traces corresponding to the selected region 902, may be displayed, along with annotation information 906 corresponding to each beat. In the illustrated example, a clinician may be able to determine that the selected region 902 corresponding to a respiratory sinus arrhythmia having an average heart rate of 60 bpm, but where intervals vary between 55 bpm and 80 bpm. This may, for instance, prompt the clinician to investigate why capture threshold increases for short intervals but for only 30 minutes in the morning. Such an investigation may involve requesting the system to present additional correlation information associated with other parameters such as, for example, diet, posture, medication, and/or the like.

FIG. 10 depicts another illustrative graphical representation 1000 of correlation information. In this example, the correlation information is associated with QRS width and average heart rate. In embodiments, a clinician may, for example, be able to glance at the graphical representation 1000 and determine, from the presented information, the occurrence of an exercise-induced bundle branch block. This information may, for instance, prompt the clinician to recommend a medication change and/or changes to CRT programming. FIG. 11 depicts another illustrative graphical representation 1100 of correlation information. In this example, the correlation information is associated with % capture and posture. In embodiments, a clinician may, for example, be able to glance at the graphical representation 1100 and determine, from the presented information, that the capture threshold changes when the subject sleeps on one side. This information may, for instance, prompt the clinician to recommend adjusting a pace amplitude or safety margin on an auto-threshold. In embodiments, the CRT device may be configured, for example, to automatically adjust a pacing amplitude or safety margin based on posture (e.g., based on a roll parameter, a pitch parameter, a yaw parameter, etc.).

FIGS. 4-11 are not intended to be limiting, but only to give illustrative examples of the types of information that may be presented, and various types of formats of presenting that information, in accordance with embodiments of the disclosure, for facilitating presenting results of an evaluation of pacing effectiveness.

Embodiments of the systems, devices, and/or processes herein additionally, or alternatively, may be utilized for using data from an IMD to identify cardiac conduction issues and patterns. For example, embodiments may include extracting higher-resolution data from an IMD to facilitate identifying cardiac conduction issues and patterns, make programming recommendations, and/or dynamically changing programming, (e.g., dynamically modifying therapy). In this manner, information from IMDs may be used to ascertain specific cardiac behaviors, the nature of anomalies, how the cardiac activity is interrelated with the IMD's operations, and/or the like.

Embodiments facilitate identifying conduction anomalies in the context of current and/or previous cardiac activity (e.g., heart rate), respiratory activity (e.g., rate), medication administration and/or change, diet change, exercise change, posture change, and/or the like. Embodiments may facilitate identifying non-capture events, fusion events, biventricular (BiV) fusion events (e.g., a hybrid of paced and intrinsic fusion), and/or pseudo-fusion events (e.g., where pacing is delivered, but the intrinsic activity is not altered). Additionally, embodiments facilitate determining a relationship of current cardiac cycle characteristics to those around the current cycle (e.g., PVCs, RSA, EI-LBBB, EI-RBBB, etc.). Embodiments facilitate characterizing a relationship of current cardiac cycle characteristics to activity, respiration rate, posture changes, and/or the like.

Embodiments may facilitate enhancing detection and treatment of various types of conduction blocks by utilizing study prescriptions to obtain data such as, for example, all of the marker data and interval data, as determined by the IMD, (e.g., the RV to RVS intervals and RV to LVS intervals, which may be used to determine rate and widening of QRS). In embodiments, because CRT typically does not promote intrinsic activity, the study prescription may instruct the IMD to periodically alter pacing to enhance the ability to obtain relevant data. Other data that may be obtained using the study prescription may include, for example, at least one EGM channel, accelerometer (e.g., all or summarized as activity above and/or below a threshold), MV (e.g., all or summarized as breaths per minute rate or apnea event determined), and/or other sensor data (e.g., heart sounds). Additionally, the detection of S4 heart sounds may be used to help determine rate dependent conduction anomalies. A sudden increase in S4-R interval may be indicative of first degree of AV block and the change of S4-R interval may be used to determine second/third AV block.

Embodiments may facilitate providing conduction anomaly analysis reports that may include, for example, rate of occurrence, EGM examples, rate vs. conduction analysis, activity vs. conduction analysis, intrinsic AV delay vs. conduction analysis, time of day vs. conduction analysis, and/or the like. In embodiments, analysis reports and/or other output may include context during occurrence of identified anomalies such as activity; HR before, during, and after; posture; change in posture; respiratory rate or phase of respiratory cycle, time of day, and/or the like. For example, embodiments facilitate providing reconstructed EGM as an aid in communicating these types of anomalies (e.g., widening QRS due to activity, respiration cycle changes, and/or other influences). The system may also report recommendations for adjusting therapy, may facilitate remote programming of the IMD, may provide alerts to users (e.g., clinicians and/or patients), and/or the like. In embodiments, instead of, or in addition to, executing the study prescription in response to detection of a trigger event, the study prescription (or various modifications thereof) may be executed as part of routine between implantation of an IMD and discharge of the patient from the medical facility.

Figure 12:
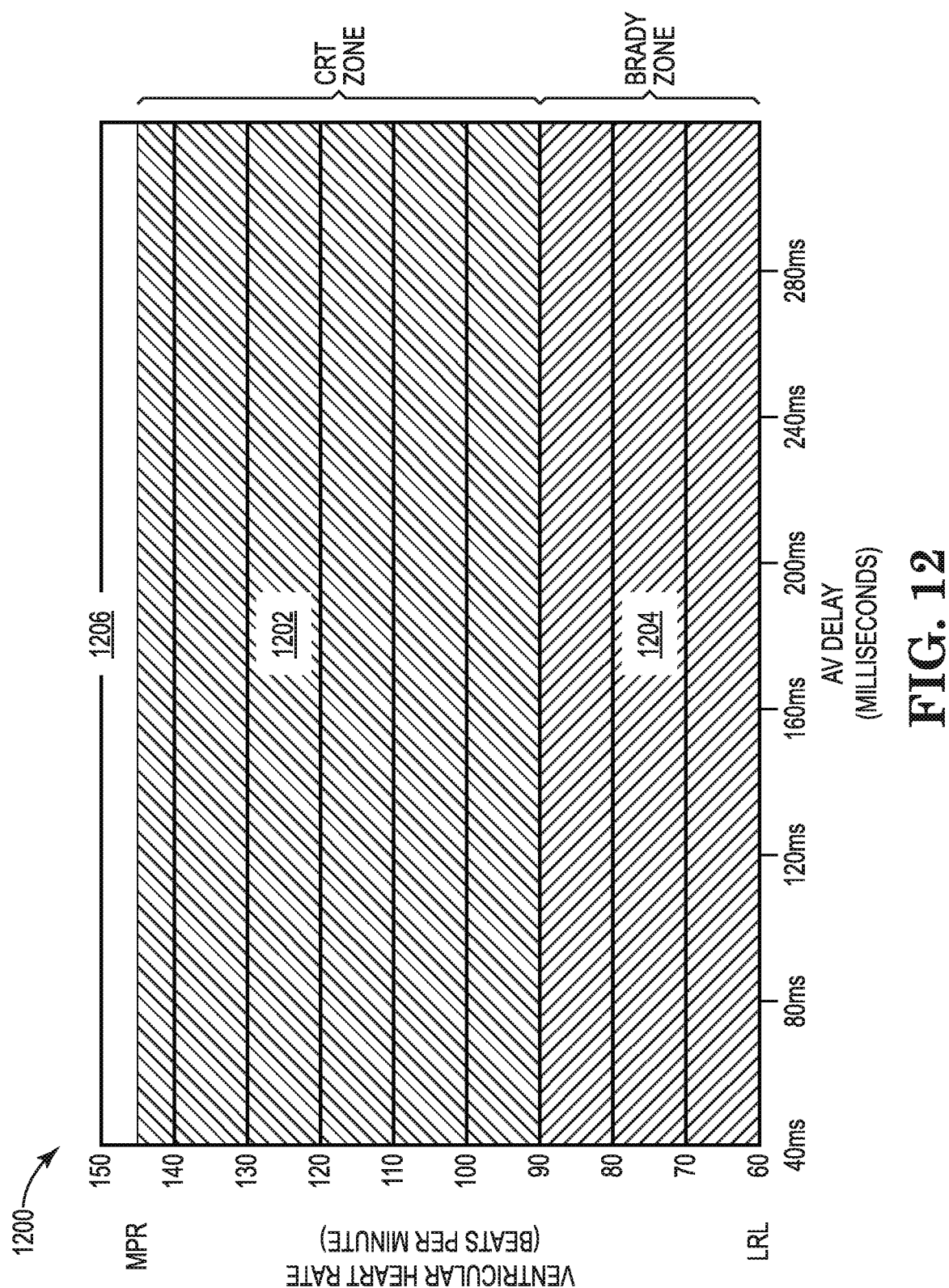
FIG. 12 depicts illustrative pacing zones, in accordance with embodiments of the disclosure.

In embodiments, a conduction anomaly analysis study prescription may be implemented to facilitate tailoring pacing (e.g., timing, electrode location, etc.) therapy to the subject. For example, the study prescription may facilitate recommending CRT if a widening QRS heart failure (HF) is detected, and may be used to enhance physiologic demand driven pacing such as that described in U.S. Pat. No. 8,600,504, assigned to Cardiac Pacemakers, Inc., the entirety of which is hereby expressly incorporated herein by reference. Additionally, as shown in FIG. 12, embodiments may include a study prescription that facilitates establishing pacing zones. The x-axis represents AV delay measured in milliseconds (ms). The y-axis represents ventricular heart rate measured in beats per minute (bpm). The study prescription may facilitate creating a CRT zone 1202 between a brady zone 1204 and a tachy zone 1206, with ranges determined, for example, by where EI-LBBB or EI-RBBB begins. For example, the brady zone 1204 may extend between the lower rate limit (LRL) to the CRT zone 1202, which may extend from the lower end of the CRT zone 1202 to the maximum pacing rate (MPR). The brady/CRT pacing zones may be implemented using two programmable AV Delay ranges, BiV trigger for senses in the CRT zone, and/or the like. In embodiments, the CRT zone may be activity-based (using output from, e.g., an accelerometer, an MV component, etc.), or posture-based, instead of, or in addition to, being rate-based. A wide QRS detector may be used, in embodiments, to automatically set the lower end of the CRT zone 1202. Examples of the wide QRS detector are described, for example, in U.S. Pat. No. 8,600,504.

Figure 13:
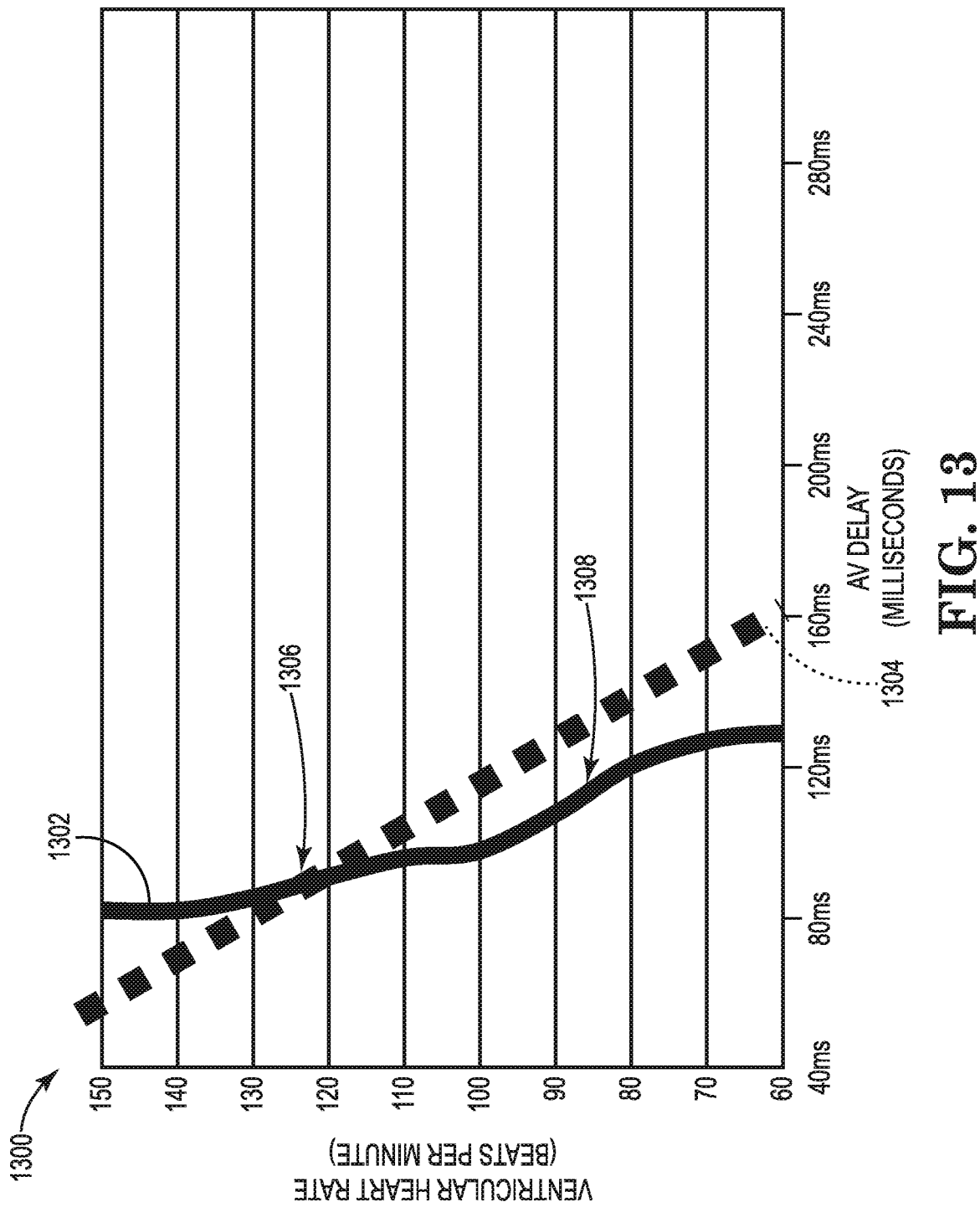
FIG. 13 shows an example of a plot of AV delay versus ventricular heart rate, including a representation of a dynamic programmed AV delay, in accordance with embodiments of the disclosure.

In embodiments, a study prescription may also facilitate altering paced AV delay slope to promote intrinsics near LRL and promote BiV pacing when needed, and/or the like. FIG. 13 shows an example of a plot of AV delay versus ventricular heart rate. The x-axis represents AV delay measured in milliseconds (ms). The y-axis represents ventricular heart rate measured in beats per minute (bpm). The curve 1302 represents the patient's intrinsic AV delay at various ventricular heart rates. The line 1304 represents the dynamic programmed AV delay. Embodiments of a method for using a programmable AV delay slope may include setting a maximum rest pacing rate to be greater than intrinsic AV delay (at rest) to promote intrinsic conduction at rest; setting a minimum active pacing rate to be less than an intrinsic AV delay (active) such that the curve 1304 representing the programmed AV delay intersects with the intrinsic AV delay curve 1302 at the heart rate where EI-LBBB initiates 1306. In this example, the QRS width might be classified as "narrow" where the programmed AV delay is greater than the intrinsic AV delay 1308. This process may, in embodiments, be automated using data from the analysis of conduction anomalies (e.g., the study prescription).

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A cardiac rhythm management system, comprising:
at least one sensing component configured to obtain a first physiological parameter signal, an indication of a cardiac response to a stimulation therapy, and temporal information corresponding to the first physiological parameter signal and the cardiac response; and
at least one processor configured to:
receive the first physiological parameter signal, the indication of the cardiac response, and the temporal information; and
classify the cardiac response into a first cardiac response class to generate a classified cardiac response, the first cardiac response class comprising one of a plurality of cardiac response classes, the plurality of cardiac response classes comprising a pace-dominant response class, a non-capture response class, a fusion response class, a pseudo-fusion response class, a bi-ventricle (BiV) fusion response class, a left ventricle (LV) only BiV capture response class, and a right ventricle (RV) only BiV capture response class;
determine a correlation, based on the temporal information, between the first physiological parameter signal and the classified cardiac response;
cause a display device to present a representation of the correlation; and
generate a therapy programming change recommendation that is different for different cardiac response classes of the plurality of cardiac response classes.

2. The system of claim 1, wherein the first physiological parameter comprises at least one of a heart rate, a respiration rate, a blood pressure, a posture, an S1 heart sound, an S2 heart sound, and a cardiac interval within a cardiac cycle.

3. The system of claim 2, the first physiological parameter comprising an S1 heart sound, wherein the processor is configured to classify the cardiac response based on at least one of a morphology of the S1 heart sound and an intensity of the S1 heart sound.

4. The system of claim 2, the first physiological parameter comprising an S2 heart sound, wherein the processor is configured to:
determine an S2-R interval; and
classify the cardiac response based on the determined S2-R interval.

5. The system of claim 1, further comprising at least one additional sensing component configured to obtain a second physiological parameter signal, wherein the at least one processor is further configured to verify the classification of the cardiac response based on the second physiological parameter signal.

6. The system of claim 5, wherein the second physiological parameter comprises at least one of an S1 heart sound and an S2 heart sound.

7. The system of claim 1, wherein the processor is further configured to:
receive a plurality of additional indications of a plurality of additional cardiac responses and the first physiological parameter signal;
classify each of the plurality of additional cardiac responses to generate a plurality of additional classified cardiac responses;
correlate each of the plurality of additional classified cardiac responses with the first physiological parameter signal to generate a plurality of additional correlations; and
cause the display device to present a representation of the plurality of additional correlations.

8. The system of claim 7, wherein the representation of the plurality of additional correlations comprises a graph including representations of the first physiological parameter signal and the plurality of additional classified cardiac responses by time of day.

9. A cardiac rhythm management system, comprising:
at least one sensing component configured to obtain a heart sound signal, a plurality of indications of a plurality of cardiac responses to a stimulation therapy, and temporal information corresponding to the heart sound signal and the cardiac responses; and
at least one processor configured to:
receive the heart sound signal, the plurality of indications of the plurality of cardiac responses, and the temporal information; and
classify each of the plurality of cardiac responses into one of a plurality of cardiac response classes to generate a plurality of classified cardiac responses;
determine a correlation, based on the temporal information, between the heart sound signal and the plurality of classified cardiac responses;
cause a display device to present a representation of the correlation; and
generate a therapy change recommendation that is different for different cardiac response classes of the plurality of cardiac response classes.

10. The system of claim 9, the plurality of cardiac response classes comprising a pace-dominant response class, a non-capture response class, a fusion response class, a pseudo-fusion response class, a bi-ventricle (BiV) fusion response class, a left ventricle (LV) only BiV capture response class, and a right ventricle (RV) only BiV capture response class.

11. The system of claim 9, wherein the heart sound signal comprises at least one of an S1 heart sound signal and an S2 heart sound signal.

12. The system of claim 11, wherein the heart sound signal comprises an S1 heart sound signal, the processor further configured to determine a morphology of the S1 heart sound signal and/or an intensity of the S1 heart sound signal, wherein the processor is configured to classify each of the plurality of cardiac responses based on the morphology of the S1 heart sound signal and/or the intensity of the S1 heart sound signal.

13. The system of claim 11, wherein the heart sound signal comprises an S2 heart sound signal, wherein the processor is configured to:
determine an S2-R interval; and
classify the cardiac response based on the determined S2-R interval.

14. The system of claim 9, wherein the at least one processor is further configured to generate, based on at least one of the classified cardiac response and the correlation, a therapy programming change recommendation.

15. A method of evaluating an effectiveness of a pacing therapy, the method comprising:
obtaining a first physiological parameter signal, an indication of a cardiac response to a stimulation therapy, and temporal information corresponding to the first physiological parameter signal and the cardiac response, wherein the first physiological parameter comprises at least one of a heart rate, a respiration rate, a blood pressure, a posture, an S1 heart sound, and an S2 heart sound;

obtaining a second physiological parameter signal;

classifying the cardiac response into a first cardiac response class to generate a classified cardiac response, the first cardiac response class comprising one of a plurality of cardiac response classes, the plurality of cardiac response classes comprising a pace-dominant response class, a non-capture response class, a fusion response class, a pseudo-fusion response class, a bi-ventricle (BiV) fusion response class, a left ventricle (LV) only BiV capture response class, and a right ventricle (RV) only BiV capture response class;

verifying the classification of the cardiac response based on the second physiological parameter signal;

determining a correlation, based on the temporal information, between the first physiological parameter signal and the classified cardiac response;

causing a display device to present a representation of the correlation; and generating a therapy change recommendation that is different for different cardiac response classes of the plurality of cardiac response classes.

16. The method of claim 15, wherein the second physiological parameter comprises at least one of an S1 heart sound and an S2 heart sound.

17. The method of claim 15, further comprising:

obtaining a plurality of additional indications of a plurality of additional cardiac responses and the first physiological parameter signal;

classifying each of the plurality of additional cardiac responses to generate a plurality of additional classified cardiac responses;

correlating each of the plurality of additional classified cardiac responses with the first physiological parameter signal to generate a plurality of additional correlations; and causing the display device to present a representation of the plurality of additional correlations.

* * * * *